United States Patent [19]

Mádi-Szabó et al.

[11] Patent Number: 4,705,779

[45] Date of Patent: Nov. 10, 1987

[54] PHARMACEUTICAL COMPOSITIONS OF ANTI-PANCREATIC INFLAMMATORY EFFECT

[75] Inventors: László Mádi-Szabó; Margit Morvai; Eva Horváth née Fehér, all of Budapest; Sándor Janscó, Debrecen; Piroska Tamási, Debrecen; Kovács, István, Debrecen; Kiss née Loss, Ilona Mária, Debrecen; György Bacsa, Debrecen; Mária Kubala née Papp; Magdolna Bene née Horváth, both of Tiszavasvári, all of Hungary

[73] Assignee: Biogal Gyogyszergyar of Debrecen and Alkaloida Vegyeszeti Gyar of Tiszavasvari, Tiszavasvari, Hungary

[21] Appl. No.: 681,887

[22] PCT Filed: Mar. 12, 1984

[86] PCT No.: PCT/HU84/00016

§ 371 Date: Nov. 8, 1984

§ 102(e) Date: Nov. 8, 1984

[87] PCT Pub. No.: WO84/03442

PCT Pub. Date: Sep. 13, 1984

[30] Foreign Application Priority Data

Mar. 11, 1983 [HU] Hungary .................................. 842/83

[51] Int. Cl.$^4$ ...................... A61K 31/70; A61K 31/53; A61K 31/22

[52] U.S. Cl. ...................................... 514/27; 514/214; 514/546

[58] Field of Search .................. 514/27, 241, 183, 546

[56] References Cited

PUBLICATIONS

Merck Index, 10th Edition, Compound 9590 & 780.
Merck Index, II 759 & 1240, 9th Ed., 1974.

*Primary Examiner*—J. R. Brown
*Assistant Examiner*—John W. Rollins, Jr.
*Attorney, Agent, or Firm*—Karl F. Ross; Herbert Dubno; Jonathan Myers

[57] ABSTRACT

The present invention relates to pharmaceutical compositions comprising 3-dimethylamino-7-methyl-1,2-(n-propylmalonyl)-1,2-dihydro-1,2,4-benzotriazine and at least one of a factor of Vitamine P and/or (+)-2-(3,4-dihydroxyphenyl)-3,5,7-cromanetriole as active ingredients, a process for preparing the same and a method for treating pancreatic inflammations with the said composition.

The pharmaceutical compositions according to the invention are useful for the treatment of pancreatic inflammations.

5 Claims, No Drawings

PHARMACEUTICAL COMPOSITIONS OF ANTI-PANCREATIC INFLAMMATORY EFFECT

TECHNICAL FIELD

The present invention relates to synergistic pharmaceutical compositions of anti-pancreatic inflammatory effect, a process for preparing the same and a method for treating pancreatic inflammations.

In particular, the invention is directed to pharmaceutical compositions comprising one or more active ingredients of antiphlogistic and vascular effect, a process for preparing the same and a method for treating pancreatic inflammations with the said compositions.

BACKGROUND ART

In the last two decades the chronic inflammatory diseases of the pancreas appeared to cause increased clinical problems. This phenomenon is accompanied on one hand by the increased number of patients, on the other hand by the increased number of diagnostic methods. These facts are referred to in the following publication: Marks, J. N., Bank, S., Louw, I. H.: Leber, Magen, Darm. 6 257, 1976.

It is known in the art that the pancreatic inflammatory processes show specific features (Papp, M.: Congress of the Hungarian Gastroent. Society, Keszthely, Hungary, 1981).

The inflammation is of either ductalic or parenchimic feature, the deterioration of parenchyma, progressive histolysis, fibrotizing processes and cicatrization occur soon. The constant presence of the free digestive enzymes assuring the autoperpetuation is induced by the inflammatory mechanism, the oedematic processes and the trophic disorders to a high degree. Besides the inflammed oedema the compression of the subcapsular lymphatics also diminishes the microcirculation. G. Kaiser's and G. Hommel's observation is also of great importance. According to their report the decreasing demand for blood supply of the pancreas mass under deterioration induces adaptive intimafibrosis in the small blood-vessels. This process further reduces the blood amount rushing to the gland and it can be the basis of further atrophy, [Kaiser, G., Hommel, G.: Morphometrisch-statistische Analyse der Pankreasarterien bei chronischer Pankreatitis. Virchows Arch (Pathol. Anat.) 365 103 (1975)].

In spite of the above theoretical considerations there are no available pharmaceutical compositions of satisfactory effectiveness for the treatment of pancreatic inflammations until now. In order to relieve the patients of the unpleasant effect of the chronic inflammations the medical treatment is limited to administering an enzyme along with a particular diet. Such enzyme preparations are e.g. Dipankrine, Cotasym Forte or Panpur.

DISCLOSURE OF THE INVENTION

The aim of our research work was to develop a pharmaceutical composition which is suitable for the effective treatment of patients suffering from pancreatic inflammations. According to our observation from the group of antiinflammatory agents the steroids would rather induce recidiva while the prostaglandine antagonists are powerless.

Surprisingly we have found that the pharmaceutical compositions containing 3-dimethylamino-7-methyl-1,2-(n-propylmalonyl)-1,2-dihydro-1,2,4-benzotriazine and at least one of the Vitamin P factors and/or (+)-2-(3,4-dihydroxyphenyl)-3,5,7-cromanetriole as active ingredients are effective against pancreatic inflammations.

As a factor of Vitamin P a water soluble rutine derivative, preferably 3′,4′,7-tris($\beta$-hydroxyethyl)-rutoside, can be used.

The weight ratio of 3-dimethylamino-7-methyl-1,2-(n-propylmalonyl)-1,2-dihydro-1,2,4-benzotriazine and a factor of Vitamine P is between 2:1 to 1:1 in the compositions of the invention.

The weight ratio of 3-dimethylamino-7-methyl-1,2-(n-propylmalonyl)-1,2-dihydro-1,2,4-benzotriazine and (+)-2-(3,4-dihydroxyphenyl)-3,5,7-cromanetriole varies within the range of 2:1 to 1:1 in the compositions of the invention.

The compositions according to the invention contain suitably 60 to 300 mg. of 3-dimethylamino-7-methyl-1,2-(n-propylmalonyl)-1,2-dihydro-1,2,4-benzotriazine and altogether 60 to 300 mg. of a factor of Vitamin P and/or (+)-2-(3,4-dihydroxyphenyl)-3,5,7-cromanetriole per dosage unit.

The pharmaceutical compositions according to the invention contain optionally one or more known antibiotics and/or trace elements and/or vitamins in association with carrier(s), excipient(s) and diluent(s) conventionally used in the preparation of pharmaceutical compositions.

As antibiotics Penicillin V or Tobramycin are preferred.

The compositions of the invention contain optionally as vitamins e.g. magnesium ascorbate, ascorbic acid or other conventionally used vitamins.

As carriers or diluents those conventionally used, e.g. talc, calcium carbonate, magnesium stearate, starch, dextrine, water, physiological saline solution or polyethylene glycols can be used.

The compositions according to the invention contain as excipients conventional excipients, for example emulsifying agents, disintegrating agents or sweeteners.

Preferred pharmaceutical forms of the present invention are solid forms such as tablets, pills, capsules, dragees, granules, or liquid forms, such as solutions, suspensions, emulsion, syrups, injections, infusion solutions.

These compositions are administered orally, by intravenous or subcutaneous injections or by infusions.

Clinical results obtained by the administration of 3-dimethylamino-7-methyl-1,2-(n-propylmalonyl)-1,2-dihydro-1,2,4-benzotriazine (Azapropazonum)

As it is well known from pharmacological and pharmaco-kinetical experiments, Azapropazonum can be well absorbed from the duodenum and is well distributed in the extracellular space. In inflamed tissues it enriches to 3 to 8-fold amount calculated for the oedemic liquids.

It is not decomposed in the organismus, it is not metabolized in the liver and it evacuates with the urine. The ulcerogenic effect of the compound can be neglected, liver and medulla damaging effect is not observed, and it does not possess teratogenic and carcinogenic effects. It does not influence detectably the function of the organs, does not effect the increase in the body weight, the composition of the urine and the blood. It has a slight influence on the anabolic function of the cells, does not change either the cell production or the specific synthesis thereof, thus it does not retard the mucopolysaccharide production and therefore does not interfere with the reparation process. However, it restrains the catabolic anabolic processes by its effect on the mediators of the inflammation. It blocks the course of the inflammatory process on the level of the deliberation or the function of the lysosomalic enzymes.

The results of the treatments with Azapropazonum as active ingredients are enclosed by Table 1.

Having demonstrated that the acute toxicity of Azapropazonum is not increased in the presence of Hydroxyrutosidea or Catechin, further experiments were carried out.

In the first step of these experiments Hydroxyrutoside or Catechin were administered to the patients alone. The results are shown in Tables 2 and 3.

TABLE 2

| Number of patients from 20 patients | Pathography | | | | | |
|---|---|---|---|---|---|---|
| | cholecysto-pancreatitis (with stones) | cholangiopancr. (st. p. cholecyst-ectomiam) | chol. pancr. + diabetes | chol. pancr. + ps. cysta | Panc. chr. alc. | Panc. chr. + ps. cysta |
| men: 5 | 1 | — | — | — | 3 | 1 |
| women: 15 | 5 | 5 | 2 | 1 | 2 | — |
| clinical effect | | | | | | |
| insignificant 6 | 2 | 2 | — | 1 | — | 1 |

Daily 3 × 300 mg. of Hydroxyrutosidea were administered orally.
The treatment was carried out for 12 weeks.

TABLE 3

| Number of patients from 20 patients | Pathography | | | | | |
|---|---|---|---|---|---|---|
| | cholecysto-pancreatitis (with stones) | cholangiopancr. (st. p. cholecyst-ectomiam) | chol. pancr. + diabetes | chol. pancr. + ps. cysta | Panc. chr. alc. | Panc. chr. + ps. cysta |
| men: 7 | 2 | 1 | — | — | 3 | 1 |
| women: 13 | 5 | 4 | 1 | 1 | 2 | 1 |
| clinical effect | | | | | | |
| insignificant 6 | 1 | 2 | — | 1 | 1 | 1 |

Daily 3 × 300 mg. of Catechin were administered orally to the patients.
The treatment was carried out for 12 weeks.

TABLE 1

| Number of patients from 20 patients | Pathography | | | | |
|---|---|---|---|---|---|
| | cholecysto-pancreatitis (with stones) | cholangiopancr. (st. p. cholecyst-ectomiam) | Chol. pancr. + diabetes | Panc. chr. alc. | Panc. chr. alc. + ps. cysta |
| men: 7 | — | 1 | 1 | 4 | 1 |
| women: 13 | 7 | 4 | 1 | 1 | — |
| clinical effect | | | | | |
| insignificant | 5 | 4 | 1 | 2 | 1 |
| medium | 2 | 1 | — | 3 | — |
| excellent | — | — | — | — | — |

Daily 3 × 300 mg. of Azapropazonum were administered orally.
The treatment was carried out for 12 weeks.

Clinical results obtained by the administration of Hydroxyrutosidea or Catechin alone and combinations according to the invention In order to increase the antiinflammatory effect, compounds of vascular effect were simultaneously tested.

Two compounds were chosen: 3',4',7-tris($\beta$-hydroxyethyl)rutoside (referred to as Hydroxyrutoside) and (+)-2-(3,4-dihydroxyphenyl)-3,5,7-cromanetriole (referred to as Catechin).

As it is shown by the tables, the administration of Hydroxyrutosidea or Catechin alone resulted in an insignificant effect.

Surprisingly, the simultaneous administration of Azapropazonum and Hydroxyrutosidea or Azapropazonum and Catechin resulted in an unexpected effect. The anti-pancreatic inflammatory effect of Azapropazonum was highly synergyzed by the compounds of vascular effect employed in the experiments. The results are included into Table 4.

TABLE 4

| Number of patients from 50 patients | Combination of compounds applied | Pathography | | | | | | |
|---|---|---|---|---|---|---|---|---|
| | Azapropazonum + Hydroxyrutosidea | Cholecysto pancr. (with stones) | Chol. pancr. (st. p. cholecystecomiam) | Chol. angio pancr. + diabetes | Chol. angio pancr. + ps. cysta | Panc. chr. alc. | Pancr. chron. alc. + diabetes | Pancr. chron. alc. + ps. cysta |
| men: 16 | | 2 | 2 | 1 | 2 | 2 | 3 | 4 |
| women: 34 | | 10 | 10 | 6 | 2 | 5 | 1 | — |

TABLE 4-continued

| Number of patients from 50 patients | Combination of compounds applied Azapropa- zonum + Hydroxy- rutosidea | Pathography | | | | | | |
|---|---|---|---|---|---|---|---|---|
| | | Chole- cysto pancr. (with stones) | Chol. pancr. (st. p. chole- cysteco- miam) | Chol. angio pancr. + dia- betes | Chol. angio pancr. + ps. cysta | Panc. chr. alc. | Pancr. chron. alc. + diabe- tes | Pancr. chron. alc. + ps. cysta |
| clinical effect | | | | | | | | |
| insufficient | — | — | — | — | — | — | — | — |
| medium | 18 | 7 | 3 | 4 | 1 | — | 2 | 1 |
| excellent | 32 | 5 | 9 | 4 | 3 | 7 | 1 | 3 |
| men: 16 | Azapropa- | 1 | 2 | 1 | 2 | 1 | 3 | 4 |
| women: 36 | zonum + Catechin | 10 | 11 | 6 | 3 | 5 | 1 | — |
| clinical effect | | | | | | | | |
| insufficient | — | — | — | — | — | — | — | — |
| medium | 15 | 6 | 3 | 3 | 1 | 1 | — | 1 |
| excellent | 35 | 6 | 8 | 5 | 3 | 8 | 3 | 2 |

Daily 3 × 300 mg. of Azapropazonum and 3 × 300 mg. of Hydroxyrutoside or 3 × 300 mg. of Cathechin were administered to the patients. The treatment was carried out for 12 weeks in the case of both combinations.

Abbreviations applied in Tables 1 to 4:
cholangiopancr.=cholangiopancreatitis
st.p.cholecystectomiam=status post cholecystectomiam
chol.pancr.+diabetes=cholangipancreatitis+diabetes
panc.chr.alc.=pancreatitis chronica alcoholica
panc.chr.alc.+ps.cysta=pancreatitis chronica alcoholica+pancreas cysta

MODES OF CARRYING OUT THE INVENTION

The invention is illustrated by the following, non-limiting examples.

EXAMPLE 1

Composition of a tablet:
Azapropazonum: 300 mg.
Hydroxyrutoside: 300 mg.
Carrier: q.s. for a tablet

EXAMPLE 2

Composition of a tablet:
Azapropazonum: 300 mg.
Hydroxyrutoside: 150 mg.
Catechin: 150 mg.
Carrier: q.s. for a tablet

EXAMPLE 3

Composition of a tablet:
Azapropazonum: 300 mg.
Hydroxyrutoside: 150 mg.
Ascorbinic acid: 100 mg.
Carrier: q.s. for a tablet

EXAMPLE 4

Composition for a tablet:
Azapropazonum: 150 mg.
Catechin: 150 mg.
Carrier: q.s. for a tablet

EXAMPLE 5

Composition of a dragée:
Azapropazonum: 150 mg.
Hydroxyrutoside: 150 mg.
Magnesium ascorbate: 150 mg.
Penicillin V: 30 mg.
Tobramycin: 40 mg.
Carrier: q.s. for a dragée

EXAMPLE 6

Composition of a capsule:
Azapropazonum: 150 mg.
Hydroxyrutoside: 150 mg.
Carrier: q.s. for a capsule

EXAMPLE 7

Composition of a capsule:
Azapropazonum: 150 mg.
Catechin: 150 mg.
Sodium ascorbate: 30 mg.
Carrier: q.s. for a capsule

EXAMPLE 8

Composition of a drinkable liquid (drops):
Azapropazonum: 300 mg.
Hydroxyrutoside: 300 mg.
Vitamine C: 3 mg.
Diluent: q.s. 100 ml.

EXAMPLE 9

Composition of an infusion solution:
Azapropazonum: 3 g.
Folescutol: 3 g.
Vitamine C: 3 g. Dissolved in physiological saline solution, filled into infusion glasses of 0.5 or 1.0 l. volume after filtration to sterile: q.s. 1000 ml.

EXAMPLE 10

Composition of an injectable preparation:
Azapropazonum: 3 g.
Hydroxyrutoside: 3 g.
Penicillin V: 30 mg. Dissolved in physiological saline solution, filled into 2.0 to 5.0 ml. ampoulles after filtration to sterile: q.s. 1000 ml.

What we claim is:

1. A pharmaceutical composition for the treatment of inflammation of the pancreas which comprises a therapeutically effective amount of a combination of 3-dimethylamino-7-methyl-1,2-(n-propyl-malonyl)-1,2-dihydro-1,2,4-benzotriazine, and a second compound selected from the group consisting of 3',4',7-tris-(beta-hydroxyethyl)-rutoside, (+)-2-(3,4-dihydroxyphenyl)-3,5,7-cromanetriole, and mixtures thereof, wherein the weight ratio between the 3-dimethylamino-7-methyl- 1,2-(n-propylmalonyl)-1,2-dihydro-1,2,4-benzotriazine and the second compound is 2:1 to 1:1.

2. The pharmaceutical composition defined in claim 1 comprising 3-dimethylamino-7-methyl-1,2-(n-propylmalonyl)-1,2-dihydro-1,2,4-benzotriazine and 3',4',7-tris-(beta-hydroxyethyl)-rutoside in a weight ratio of 2:1 to 1:1.

3. The pharmaceutical composition defined in claim 1 comprising 3-dimethylamino-7-methyl-1,2-(n-propylmalonyl)-1,2-dihydro-1,2,4-benzotriazine and 3',4',7-tris-(beta-hydroxyethyl)-rutoside in a weight ratio of 1:1.

4. The pharmaceutical composition defined in claim 1 comprising a pharmaceutically acceptable inert carrier, diluent or excipient.

5. A method of treating pancreatic inflammation which comprises the step of administering to the patient in need of said treatment, a therapeutically effective amount of the composition defined in claim 1.

* * * * *